US006750358B2

(12) United States Patent
Petersen et al.

(10) Patent No.: US 6,750,358 B2
(45) Date of Patent: Jun. 15, 2004

(54) METHOD FOR THE PREPARATION OF CITALOPRAM

(75) Inventors: Hans Petersen, Vanoløse (DK); Michael Harold Rock, Hvidovre (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/012,025

(22) Filed: Nov. 6, 2001

(65) Prior Publication Data

US 2002/0061925 A1 May 23, 2002

Related U.S. Application Data

(63) Continuation of application No. PCT/DK99/00643, filed on Nov. 19, 1999.

(30) Foreign Application Priority Data

Jun. 25, 1999 (DK) .......................... 1999 00921

(51) Int. Cl.⁷ ............................................ C07D 307/87
(52) U.S. Cl. ...................................... 549/467
(58) Field of Search ........................... 549/467

(56) References Cited

U.S. PATENT DOCUMENTS

| | | | |
|---|---|---|---|
| 3,467,675 A | 9/1969 | Petersen et al. | 260/346.2 |
| 4,136,193 A | 1/1979 | Bogeso et al. | 424/285 |
| 4,650,884 A | 3/1987 | Bogeso | 549/467 |
| 4,943,590 A | 7/1990 | Boegesoe et al. | 415/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,162,942 A | 12/2000 | Rock et al. | 558/337 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,331,628 B1 | 12/2001 | Kondo et al. | 544/312 |

FOREIGN PATENT DOCUMENTS

| | | | | |
|---|---|---|---|---|
| DE | 100 15 280 A1 | 1/2001 | ........... | C07B/43/08 |
| EP | 0 384 392 A1 | 2/1990 | ......... | C07C/255/50 |
| EP | 1 095 926 | 5/2001 | ........... | C07C/33/46 |
| WO | 98/19511 | 5/1998 | | |
| WO | 98/19512 | 5/1998 | | |
| WO | 98/19513 | 5/1998 | | |
| WO | 98/37058 | 8/1998 | ......... | C07C/253/14 |
| WO | 99/30548 | 6/1999 | | |
| WO | 00/11926 | 3/2000 | | |
| WO | 00/12044 | 3/2000 | | |
| WO | 00/13648 | 3/2000 | | |
| WO | 00/23431 | 4/2000 | ......... | C07D/307/87 |
| WO | 00/39112 | 7/2000 | ......... | C07D/307/87 |
| WO | 00/44738 | 8/2000 | ......... | C07D/307/88 |
| WO | 01/45483 | 6/2001 | | |
| WO | 01/47877 | 7/2001 | | |
| WO | 01/66536 | 9/2001 | ......... | C07D/307/87 |

OTHER PUBLICATIONS

U.S. patent application Ser. No. 09/794,762, filed Feb. 26, 2001.

U.S. patent application Ser. No. 09/794,755, filed Feb. 26, 2001.

U.S. patent application Ser. No. 09/830,109, filed Oct. 19, 1999 (International filing date).

U.S. patent application Ser. No. 09/888,067, filed Jun. 22, 2001.

U.S. patent application Ser. No. 09/891,874, filed Jun. 25, 2001.

U.S. patent application Ser. No. 09/917,180, filed Jul. 27, 2001.

U.S. patent application Ser. No. 09/692,653, filed Oct. 19, 2000.

U.S. patent application Ser. No. 09/930,110, filed Aug. 14, 2001.

U.S. patent application Ser. No. 09/977,920, filed Oct. 15, 2001.

U.S. patent application Ser. No. 10/012,054, filed Nov. 6, 2001.

U.S. patent application Ser. No. 10/035,005, filed Dec. 20, 2001.

U.S. patent application Ser. No. 10/046,126, filed Jan. 8, 2002.

Levy, L.F., "4–Aminophthalide and Some Derivatives", *J. Chem. Soc.* pp. 867–870 (1931).

Tirouflet J., "Phtalide Substitutes en 5", *Bull. Soc. Sci. de Bretagne* 26:35–43 (1951).

(List continued on next page.)

*Primary Examiner*—Bernard Dentz
(74) *Attorney, Agent, or Firm*—Darby & Darby

(57) ABSTRACT

Method for the preparation of citalopram comprising reaction of a compound of Formula (IV)

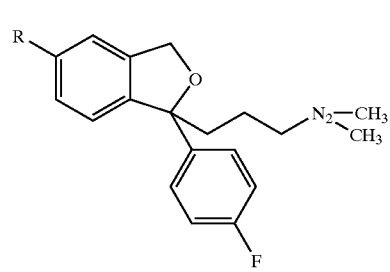

Formula IV wherein R is Cl or Br with a cyanide source in the presence of a nickel catalyst and isolation of the corresponding 5-cyano compound, i.e. citalopram.

14 Claims, No Drawings-

OTHER PUBLICATIONS

Bigler, Allan et al., "Quantitative Structure–activity Relationships in a Series of Selective 5–HT uptake inhibitors," *Eur. J. Med. Chem.* 3:289–295 (1997).

Forney L., "Reaction of Terephthalic Acid with Formaldehyde in Sulfur Trioxide Media," *J. Org. Chem.* 35:1695–1696 (1970).

Dordor et al., "Reaction of Oxazolines with Phosphorus Oxychloride," *Tetrahedron Letters* 24:1437–1440 (1983).

Barton et al., *Comprehensive Organic Chemistry. The Synthesis and Reactions of Organic Compounds,* vol. 2, pp. 1024–1025.

Sakakibara, Yasumasa, et al., "The Cyanation of Aromatic Halides Catalyzed by Nickel(0) Complexes Generated in Slltu. I. General Scope and Limitations," *Bull. Chem. Soc. Jpn.* 61:1985–1990 (1988).

Semmelhack, M.F. et al., "Reaction of Aryl and Vinyl Halldes with Zerovalent Nickel—Preparative Aspects and the Synthesis of Alnusone," *J. Am. Chem. Soc.* 103: 6460–6471 (1981).

Tsou, T.T. et al., "Mechanism of Oxidative Addition. Reaction of Nickel(0) Complexes with Aromatic Halides," *J. Am. Chem. Soc.* 101, 21: 6319–6332 (1979).

METHOD FOR THE PREPARATION OF CITALOPRAM

This application is a continuation of International Application Serial No. PCT/DK99/00643 filed Nov. 19, 1999.

The present invention relates to a method for the preparation of the well known antidepressant drug citalopram, 1-[3-(dimethylamino)propyl]-1-(4-fluorophenyl)-1,3-dihydro-5-isobenzofurancarbonitrile.

BACKGROUND OF THE INVENTION

Citalopram is a well known antidepressant drug that has now been on the market for some years and has the following structure:

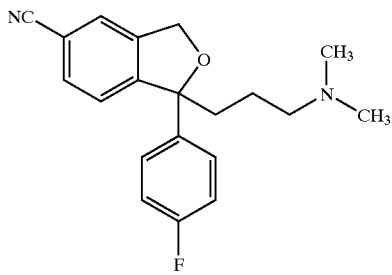

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel, *Prog. Neuro-Psychopharmacol. & Biol. Psychiat.*, 1982, 6, 277–295 and A. Gravem, *Acta Psychiatr. Scand.*, 1987, 75, 478–486. The compound has further been disclosed to show effects in the treatment of dementia and cerebrovascular disorders, EP-A 474580.

Citalopram was first disclosed in DE 2,657,013 corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

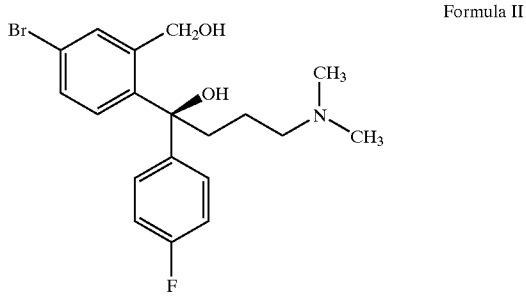

Formula II in the presence of a dehydrating agent and subsequent exchange of the 5-bromo group with cyano using cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884 according to which an intermediate of the formula

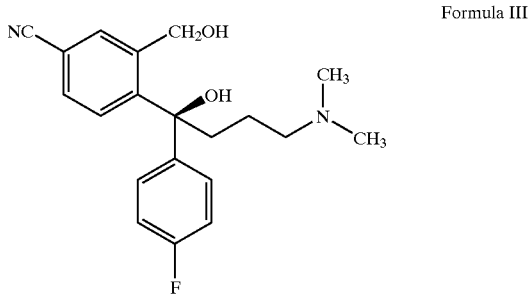

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in International patent application Nos. WO 98019511, WO 98019512 and WO 98019513. WO 98019512 and WO 98019513 relate to methods wherein a 5-amino-, 5-carboxy- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98019511 discloses a process for the manufacture of citalopram wherein a (4-substituted-2-hydroxymethylphenyl-(4-fluorphenyl)methanol compound is subjected to ring closure and the resulting 5-substituted 1-(4-fluorophenyl)-1,3-dihydroisobenzofuran converted to the corresponding 5-cyano derivative which is alkylated with a (3-dimethylamino)propylhalogenide in order to obtain citalopram.

Finally, methods of preparing the individual enantiomers of citalopram are disclosed in U.S. Pat. No. 4,943,590 from which it also appears that the ring closure of the intermediate of Formula III may be carried out via a labile ester with a base.

With respect to the above methods for the preparation of citalopram the process comprising exchange of the 5-bromo group with cyano proved not to be very convenient in commercial scale, since it was the yield was rather low, the product was impure and in particular that it was difficult to separate the resulting citalopram from the corresponding 5-bromo compound.

It has now been found that citalopram may be obtained in a high yield as a very pure produce by a new catalytic process in which 5-bromo or 5-chloro is exchanged with 5-cyano in 1-[3-(dimethylamino)propyl]-1-(4-fluorophenyl)-1,3-dihydro-isobenzofuran thus avoiding the extensive work up of the old cyanide exchange process.

SUMMARY OF THE INVENTION

Accordingly, the present invention relates to a novel method for the preparation of citalopram comprising reaction of a compound of Formula IV

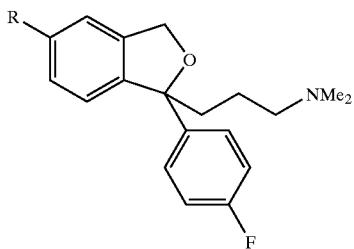

Formula IV wherein R is Cl or Br with a with a cyanide source, for example KCN, NaCN or (R')$_4$NCN where (R')$_4$ indicates four groups which may be the same or different and are selected from hydrogen and straight chain or branched C$_{1-6}$ alkyl, in the presence of a nickel catalyst and isolation of the corresponding 5-cyano compound, i.e. citalopram

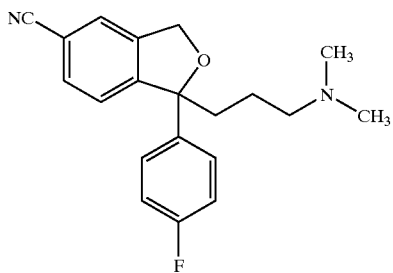

Formula I as the base or a pharmaceutically acceptable salt thereof.

In a further aspect the invention relates to the above process in which the compound of Formula IV is the S-enatiomer.

In yet another aspect, the present invention relates to an antidepressant pharmaceutical composition comprising citalopram manufactured by the process of the invention.

By the process of the invention citalopram is obtained as a pure product in high yield thus reducing costly purification processes. Furthermore, the reaction may be carried out in more convenient solvents, at a low temperature and at a low excess of CN$^-$ compared to the known cyano exchange process. The process has environmental advantages in that it only uses small amounts of heavy metals. Finally, this process gives an improved crystalline product enabling easy conversion to desired salts.

The cyanide source used may be any useful source. Preferred sources are KCN, NaCN or (R')$_4$NCN where (R')$_4$ is as defined above. The cyanide source is used in a stoichiometric amount or in excess, preferably 1–2 equivalents are used per equivalent starting material of Formula IV. (R')$_4$N$^+$ may conveniently be (Bu)$_4$N$^+$. The cyanide compound is preferably NaCN or KCN or Zn(CN)$_2$.

The nickel catalyst may be any suitable Ni(0) or Ni(II) containing complex which acts as a catalyst, such as Ni(PPh$_3$)$_3$, (o-aryl)-Ni(PPh$_3$)$_2$Cl, etc. The nickel catalysts and their preparation are described in WO 96/11906, EP-A-613720 or EP-A-384392.

In one embodiment of the invention the reaction is carried out in the presence of a catalytic amount of Cu$^+$ or Zn$^{2+}$.

In a particularly preferred embodiment a Nickel(0) complex is prepared in situ before the cyanation reaction by reduction of a Nickel(II) precursor such as NiCl$_2$ or NiBr$_2$ by a metal, such as zinc, magnesium or mangan in the presence of excess of complex ligands, preferably triphenylphosphin.

The Ni-catalyst is conveniently used in an amount of 0.5–10, preferably 2–6, most preferably about 4–5 mol %.

Catalytic amounts of Cu$^+$ and Zn$^{2+}$, respectively, means substoichiometric amounts such as 0.1–5, preferably 1–3%. Any convenient source of Cu$^+$ and Zn$^{2+}$ may be used. Cu$^{2+}$ is conveniently used as the Zn(CN)$_2$ salt or formed in situ by reduction of a nickel (II) compounds using zinc.

In a preferred embodiment of the invention, R is chloro.

In a particularly preferred embodiment of the invention a compound of Formula IV wherein R is Cl is reacted with NaCN or KCN in the presence of a Ni(PPh$_3$)$_3$ which is preferably prepared in situ as described above The intermediate of Formula IV wherein R is bromo or chloro may be prepared from bromo- and chlorophthalide, respectively, as described in DE 2,657,013 and the corresponding U.S. Pat. No. 4,136,193.

The reaction may be performed in any convenient solvent, preferably acetonitril, propionitrile, THF and ethylacetate.

Other reaction conditions, solvents, etc. are conventional conditions for such reactions and may easily be determined by a person skilled in the art.

The compound of general Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as ethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting maschine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, etc.

EXAMPLES

The invention is further illustrated by the following examples.

Example 1

Citalopram, Oxalate

Under a nitrogen atmosphere a mixture of $NiCl_2$ (0.077 g, 0.006 mol) and triphenylphosphine (0.63 g, 0.0024 mol) in acetonitrile (50 ml)was heated at reflux for 45 minutes. After cooling to room temperature zinc powder was added (0.39 g, 0.006 mol) at stirred for 15 minutes before a solution of 1-(4'-fluorophenyl)-1-(3-dimethylaminopropyl)-5-chlorophtalane (5.0 g, 0.015 mol) in acetonitrile (25 mL) was added. After stirring for a further 10 minutes NaCN (0.32 g, 0.0065 mol) was added and the reaction heated at reflux overnight, cooled, diluted with diethyl ether, and then filtered through celite. The filtrate was washed with brine, dried ($MgSO_4$) and concentrated under reduced pressure. The residue was dissolved in acetone (50 mL) and a solution of oxalic acid (1.35 g, 0.015 mol) in acetone 10 mL) was added with stirring. The Citalopram oxalate was isolated by filtration, then recrystalized from ethanol and dried in vacco to pure citalopram, oxalate (3.4 g, 55%).

What is claimed is:

1. A method for the preparation of citalopram comprising reaction of a compound of Formula IV

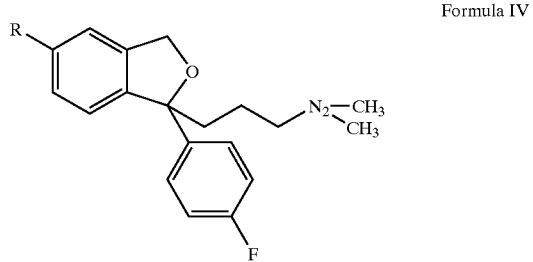

Formula IV wherein R is Cl or Br with a cyanide source in the presence of a nickel catalyst and isolation of the corresponding 5-cyano compound citalopram

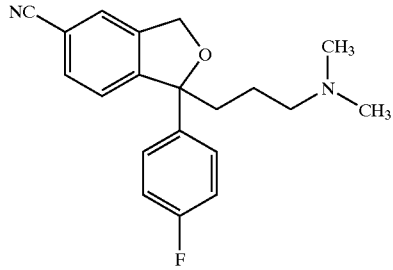

Formula I as the base or a pharmaceutically acceptable salt thereof.

2. The method of claim 1, wherein R is chloro.

3. The method of claim 1, wherein the cyanide source is KCN, NaCN, $Zn(CN)_2$ or $(R')_4NCN$ where $(R')_4$ indicates four groups which may be the same or different and are selected from hydrogen and straight chain or branched $C_{1-6}$ alkyl.

4. The method of claim 1, wherein the cyanide source is NaCN or KCN.

5. The method of claim 1, wherein the nickel catalyst is $Ni(PPh_3)_3$ or $(\sigma\text{-aryl})\text{-}Ni(PPh)_2Cl$.

6. The method of claim 1, wherein the nickel catalyst is a nickel(0) complex prepared in situ before the cyanation reaction by reduction of a nickel(II) precursor by a metal in the presence of an excess of complex ligands.

7. The method of claim 6, wherein the metal is selected from the group consisting of zinc, magnesium or manganese.

8. The method of claim 6, wherein the nickel(II) precursor is $NiCl_2$, the metal is zinc, and the complex ligands are triphenylphosphines.

9. The method of claim 1, wherein a compound of Formula IV wherein R is Cl is reacted with NaCN or KCN in the presence of a $Ni(PPh_3)_3$ catalyst.

10. The method of claim 1, wherein the $Ni(PPh_3)_3$ is prepared in situ before the cyanation reaction by reduction of $NiCl_2$ by zinc, in the presence of an excess of complex triphenylphosphine ligands.

11. The method of claim 1, wherein the reaction is carried out in the presence of a catalytic amount of $Cu^+$.

12. The method of claim 11, wherein the catalytic amount of $Cu^+$ is in the form of CuI.

13. The method of claim 1 wherein the reaction is carried out in the presence of a catalytic amount of $Zn^{2+}$.

14. The method of claim 1, wherein the compound of Formula IV is the S-enantiomer.

* * * * *